US008101202B2

(12) United States Patent
Branham et al.

(10) Patent No.: US 8,101,202 B2
(45) Date of Patent: Jan. 24, 2012

(54) GENTLE PROCESS FOR CONVERSION OF CYSTINE IN KERATIN-CONTAINING MATERIALS TO LANTHIONINE

(75) Inventors: Keith Edward Branham, Pelham, AL (US); James Perry English, Chelsea, AL (US); Donald R. Cowsar, Savannah, GA (US)

(73) Assignee: Keraplast Technologies, Ltd, San Antonio, TX (US)

( * ) Notice: Subject to any disclaimer, the term of this patent is extended or adjusted under 35 U.S.C. 154(b) by 898 days.

(21) Appl. No.: 11/570,402

(22) PCT Filed: Jun. 9, 2005

(86) PCT No.: PCT/US2005/020405
§ 371 (c)(1),
(2), (4) Date: Feb. 13, 2008

(87) PCT Pub. No.: WO2005/124013
PCT Pub. Date: Dec. 29, 2005

(65) Prior Publication Data
US 2008/0249451 A1    Oct. 9, 2008

Related U.S. Application Data

(60) Provisional application No. 60/578,786, filed on Jun. 10, 2004.

(51) Int. Cl.
*A61F 13/53*    (2006.01)
*C07K 14/46*    (2006.01)
*D06M 11/38*    (2006.01)

(52) U.S. Cl. .......... 424/443; 8/127.5; 8/128.1; 530/357; 602/50

(58) Field of Classification Search .................. None
See application file for complete search history.

(56) References Cited

U.S. PATENT DOCUMENTS

| 2,367,273 | A | * | 1/1945 | Hall et al. | 8/128.1 |
| 2,401,479 | A | * | 6/1946 | Hall et al. | 8/128.1 |
| 3,908,672 | A | | 9/1975 | Bore et al. | 132/7 |
| 3,971,391 | A | | 7/1976 | Bore et al. | 132/7 |
| 4,390,525 | A | | 6/1983 | Yoshioka et al. | 424/71 |
| 6,099,588 | A | * | 8/2000 | McDevitt et al. | 8/128.1 |
| 2005/0148703 | A1 | | 7/2005 | Barone et al. | 524/100 |

OTHER PUBLICATIONS

Lindley et al. The Action of Alkalis on Wool. Biochemical Journal. 1945, vol. 39, pp. 17-23.*
Miro et al. Formation of Cysteic Acid by the Action of Sodium Hydroxide on Wool. Journal of the Society of Dyers and Colourists. 1969, vol. 85, No. 9, pp. 407-410.*
Horn et al., "Isolation of New Sulfur-Containing Amino Acid (Lanthionine) From Sodium Carbonate-Treated Wool," J. Biol. Chem. Mar. 1941; 138: 141-149.
Horn et al, "Isolation of Mesalanthionine From Various Alkali-Treated Proteins," J. Biol. Chem., Jun. 1942; 144:87-91.
Zviak, "The Science of Hair Care," pp. 185-187, Marcel Dekker, 1986.

* cited by examiner

*Primary Examiner* — Jeffrey E Russel
(74) *Attorney, Agent, or Firm* — Vinson & Elkins, LLP

(57) ABSTRACT

Useful materials are produced from keratin containing raw materials by a process that includes gentle lanthionization of cystine disulfide bonds. Hydratable materials are produced for use in medical and cosmetic applications.

9 Claims, No Drawings

GENTLE PROCESS FOR CONVERSION OF CYSTINE IN KERATIN-CONTAINING MATERIALS TO LANTHIONINE

CROSS REFERENCE TO RELATED APPLICATIONS

This application is a National Stage filing of PCT/US05/20405 under 35 U.S.C. 371, filed Jun. 9, 2005, which claims benefit of priority to U.S. Provisional Application No. 60/578,786, filed Jun. 10, 2004.

BACKGROUND OF THE INVENTION

In proteins such as keratin, a cystine bond forming an intraprotein or interprotein link is characterized as R—C—S—S—C—R in which the C—R represents the cystine amino acid as part of a protein polypeptide and the two chains are joined by the S—S bond. This S—S bond can be broken by reduction of the Sulfur to S—H or it can be broken by oxidation to give a sulfonic acid residue, $SO_x$. Other possibilities include a substitution in which another sulfur containing moiety such as mercaptoethanol or thioglycolate are bonding to one or both sides of the cystine bond. Of these, all but the oxidation reaction are reversible and the cystine disulfide can be reformed. Oxidation of the sulfur blocks reformation of the cystine S—S bond. Lanthionization has been known for use in cosmetic treatments (see U.S. Pat. Nos. 3,908,672 and 3,971,391). A lanthionized disulfide loses one of the sulfur atoms and would be represented as R—C—S—C—R. This is also an irreversible reaction allowing one to control the amount of subsequent oxidation of the material.

In the case of keratin proteins, it is often desirable to manipulate the character of the cysteine sulfurs by partially oxidizing the material and then neutralizing the product to produce a hydrogel forming material. By controlling the number of oxidized sulfurs, the characteristics of the hydrogel material can also be controlled.

Lanthionization as disclosed for use in cosmetic treatments was done in an aqueous medium using hydroxide base, specifically LiOH, frequently at elevated temperatures and was applied to living human hair. The present inventors have found that application of this living hair technology to keratin containing raw materials and particularly wool fabric produced materials that were too fragile for certain applications or in some cases completely degraded. The present disclosure expands the use of lanthionization processes to a means of preparing new and improved materials for biomedical and other applications.

SUMMARY

The present disclosure provides novel keratin containing materials and methods of producing the novel materials that provide numerous advantages over previously known methods. The methods include at least partial lanthionization of cystine disulfide bonds in a controlled manner. The process may be used to lanthionize raw, animal-derived materials (for example, wool staple) or any keratin containing fabric or fabric blend. The process, when used to treat wool fabric, yields fabric with greater elasticity than the untreated fabric.

The lanthionization process offers at least the following advantages over controlled oxidation, including the conduction of lanthionization under unusually mild condition, i.e. at ambient temperature with no external agitation, and conducting the reaction under non-aqueous or semi-aqueous conditions. The process is unusually clean. The only products of the reaction are lanthionine (thioether linkages) and $H_2S$ gas. The residual $H_2S$ is removed by washing with water and by vacuum drying. The process provides the further advantage that it can be carried out continuously.

As found in the literature, keratin materials such as hair and wool may be fractionated into water soluble and water insoluble fractions. The water insoluble portion is known as β-keratin and has been referred to as "IKP" and IKP that has been ion exchanged is called "HKP" (hydratable keratin protein) by the applicants. The water soluble fraction contains a low sulfur portion and a high sulfur portion. The low sulfur portion is known as α-keratin or α-keratose when oxidized, and the high sulfur portion is known as γ-keratin.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements.

DETAILED DESCRIPTION

The present invention involves a process for the treatment of keratin-containing raw materials from mammalian sources, such raw materials including, but not limited to hair, wool, far, skin, horn, hooves, or bird feet, beaks, and feathers and any fabric composed wholly or partly of keratin, both woven and non-woven, and including blends with other natural and synthetic fibers such as cotton, nylon, rayon, silk, polyester etc. The treatment results in at least partial conversion of the disulfide groups (R—S—S—R) of the cystine residues in keratin to lanthionine residues (thioether groups, R—S—R) in a process know as lanthionization. The treatment is conducted in non-aqueous or semi-aqueous medium with a base such as a hydroxide base including but not limited to NaOH, KOH, $NH_4OH$, and the like, at ambient or subambient temperature in alcohols such as ethanol, methanol and isopropanol or in any of the polar aprotic solvents such as dimethylformamide (DMF), dimethyldisulfoxide (DMSO), N-methylpyrrolidone NMP). hexamethylphosphoramide (HMPA), and the like. The reaction medium may also contain water in varying amounts. One may control the rate or degree of lanthionization, by adjusting the water content of the reaction medium.

The replacement of the cystine residues with lanthionine results in the formation of permanent (essentially unreactive) thioether linkages (R—S—R) in place of the disulfide linkages (R—S—S—R) that can be cleaved by a number of methods. One important method of cleavage involves some existing technology that teaches the oxidation of raw animal products containing keratin (hair, wool, fur skin, horn, hooves, or bird feet, beaks, and feathers) to produce a keratin product containing sulfonic acid groups that is insoluble and may be used to produce a hydrogel material (for example, see U.S. Pat. No. 6,316,598 assigned to Keraplast Technologies, Ltd.)

The present disclosure offers an improvement over the previously disclosed methods by providing the opportunity to better control the number of sulfonic acid groups produced during the oxidation process by using lanthionization as a pretreatment. The use of the lanthionization process prior to oxidation also allows the preparation higher molecular weight (MW) keratin derivatives than those produced using oxidation alone by preserving crosslinks that would be broken by oxidation. This is true for both the soluble and insoluble keratin derivatives produced upon oxidation. Thus, the present disclosure provides the ability to form permanent thioether crosslinks that result in higher MW products, while simultaneously controlling the number of sulfonic acid residues present in the material. Using the disclosed methods (lanthionization) in conjunction with oxidation provides the opportunity to tailor biomaterials containing keratin to specific applications by controlling the MW, the degree of permanent crosslinking, and the number of sulfonic acid groups present.

Description of Preferred Embodiments of the Process

In one embodiment of a process for producing the disclosed materials, 125 g of wool staple were transferred to 1 one gallon jar, mixed with 1.5 L of 1.5% w/v KOH in ethanol (EtOH) and sealed with a lid. Care was taken to insure that the wool staple was completely covered and the mixture was allowed to stand undisturbed for approximately 16-18 hours. Next, the wool staple was isolated by vacuum filtration, washed with two 1 L portions of deionized water and transferred to a Teflon-lined glass dish. The wool staple exhibited the characteristic odor of hydrogen sulfide ($H_2S$) gas. The lanthionized wool staple was air dried for approximately 4 hours then vacuum dried for approximately 20 hours to yield the final product.

In another embodiment of the process fifteen squares (35.6 g) of fabric, worsted wool flannel, were transferred to a 1 L glass jar, mixed with 750 mL of 1.5% w/v KOH/EtOH, and sealed with a lid. The reaction was allowed to proceed approximately 20 hours. Next the fabric was isolated by gravity filtration and washed with two 800 mL portions of deionized water, wrung dry and transferred to a teflon-lined glass dish. At this time the wool fabric exhibited the characteristic odor of $H_2S$. The lanthionized worsted wool flannel was dried under vacuum to yield the final product. The lanthionized wool fabric had significantly more elasticity than the untreated fabric.

In certain embodiments, the present disclosure includes the use of keratin containing raw materials such as hair, wool, or feathers, or the use of soluble and insoluble keratin materials isolated from keratin containing raw materials. Keratin containing raw materials can be fractionated by breaking the disulfide bonds that form intramolecular or intermolecular bridges using oxidative or reductive chemistries.

The present disclosure provides methods for controlled lanthionization of the keratin materials or proteins. Lanthionization provides numerous advantages over prior methods of making and using these materials. As described above, mild lanthionization of wool fabric gives the fabric greater elasticity. In a wool blend fabric in which wool fibers run in one direction and a non-keratin material fiber runs in the perpendicular direction, then elasticity can be imparted in a single direction, for example.

In certain preferred embodiments, the lanthionization process can be used in conjunction with oxidation in the production of keratin gels or hydrogels. One of the goals in producing these materials has been the ability to control the number of cystine residues that are oxidized. This has previously been controlled by the concentration of oxidant and by reaction time and temperature. Lanthionization of a portion of the cystines blocks the lanthionine residues from further oxidation under mild conditions. The lanthionized keratin material may then be oxidized to produce cysteic acid groups from at least a portion of the remaining cystines. A preferred method of oxidation is to place the keratin material in 2% $H_2O_2$ at 100° C. for 1.5 hours, followed by vacuum filtration, washing in distilled deionized water and vacuum drying.

In a further embodiment, the lanthionized and oxidized material is ion exchanged, or contacted with an ion containing solution to allow the positively charged ions, or cations, to replace hydrogen ions, or to associate with negatively charged regions in the keratin material. Ion exchange may preferably be accomplished by placing the keratin material in a solution containing a cationic species such as ammonium, sodium, potassium, or calcium ions. A preferred solution for ion exchange of keratin materials is soaking the material in a solution of 0.1 M $NH_4OH$ for a period of about 8-12 hours.

The lanthionized/oxidized or lanthionized/oxidized/ion exchanged keratin materials when dried, or dried and ground are hydratable and form gels or hydrogels upon uptake of water. Such hydrated or hydratable materials are useful in various applications, including in medical applications such as bandages, sheets, tissue expanding materials, implants, cell scaffolding, as well as in cosmetic applications.

The hydratable quality of these materials makes them especially useful in the area of bandages or absorbents to be placed on a wound. In certain embodiments, for example, lanthionized or lanthionized and oxidized keratin proteins may be adsorbed into a cotton gauze pad for placement on a wound. The keratin material in the cotton enhances the absorbency of any liquids leaking or oozing from the wound. In addition, the keratin materials may be rehydrated with a solution containing active substances such as antibiotics, analgesics, cytokines, or growth factors, to aid the healing process. In certain embodiments, a pocket may be formed of cotton gauze and the keratin material may be contained in the pocket such that one layer of cotton gauze is placed against a wound and the other layer may be placed against an impermeable or adhesive backing to produce an absorbent bandage.

The disclosed materials may also be used in the production of transparent film materials, for example. In one embodiment, 1 gram samples of oxidized, dry and ground β-keratose or lanthionized, oxidized β-keratose are prepared on 5 inch squares of aluminum foil. Any of the samples may also be ion exchanged prior to production of the films. The granular solid is distributed as uniformly as possible, arranged in a square roughly 1.5 inches on each side. Next, the sample of each solid are treated with a solution of plasticizer, 20% w/w glycerol in methanol. The amount of plasticizer solution used may vary from 17% up to about 35% w/w. The samples are allowed to dry and then pressed in a Carver press using a load of 8,000 to 8,500 pounds at approximately 130° C. for 10 minutes. The films produced by this method are transparent to semi-transparent and somewhat flexible, and are reminiscent of skin. Such films are useful as wound coverings or implant materials, and may also be formed into three dimensional shapes for implant or bulking material applications.

Numerous advantages of the disclosed compositions and processes have been set forth in the foregoing description, as exemplified by the disclosed preferred embodiments. It will be understood by those of skill in the art, however, that changes may be made in details, particularly in matters of reagents, concentrations, and step order, that do not require undue experimentation. All such changes in materials or processes are understood to be equivalent variants of the disclosure and to fall within the spirit and scope of the invention.

The invention claimed is:

1. A bandage comprising a layer of dried, lanthionized, ion-exchanged keratin material.

2. The bandage of claim 1 comprising a layer of cotton gauze and a layer of dried, lanthionized, ion-exchanged keratin material.

3. The bandage of claim 2, comprising a second layer of cotton gauze.

4. The bandage of any of claims 1-3, further comprising a backing material.

5. The bandage of claim 1, 2, or 3, wherein the keratin material is oxidized.

6. A method of producing a hydratable keratin material comprising:
   (a) incubating a keratin protein material in a solution of 1.5% KOH in an alcohol or aprotic solvent at a temperature of 20-30° C. for a time of about 18-24 hours and removing the solvent to obtain a lanthionized keratin protein material; and
   (b) incubating the lanthionized keratin protein material in a solution of 0.1M $NH_4OH$ for a period of about 8-12 hours and drying the keratin protein material to obtain a hydratable keratin protein material.

7. The method of claim 6, wherein the keratin protein material is produced by isolating water insoluble keratin proteins from a keratin raw material.

8. The method of claim 6, further comprising incubating the keratin protein material in a solution of 2% $H_2O_2$ at 100° C. for 1.5 hours.

9. The method of claim 8, wherein the incubation in 2% $H_2O_2$ is done prior to step (a).

\* \* \* \* \*